(12) United States Patent
Rothermel (10) Patent No.: US 10,589,049 B2
(45) Date of Patent: Mar. 17, 2020

(54) FLUID CONNECTOR WITH EXHAUST VALVE

(71) Applicant: KONINKLIJKE PHILIPS N.V., Eindhoven (NL)

(72) Inventor: Justin Edward Rothermel, Monroeville, PA (US)

(73) Assignee: Koninklijke Philips N.V., Eindhoven (NL)

(*) Notice: Subject to any disclaimer, the term of this patent is extended or adjusted under 35 U.S.C. 154(b) by 893 days.

(21) Appl. No.: 15/105,589

(22) PCT Filed: Dec. 3, 2014

(86) PCT No.: PCT/IB2014/066541
§ 371 (c)(1),
(2) Date: Jun. 17, 2016

(87) PCT Pub. No.: WO2015/092589
PCT Pub. Date: Jun. 25, 2015

(65) Prior Publication Data
US 2016/0310688 A1    Oct. 27, 2016

Related U.S. Application Data

(60) Provisional application No. 61/917,611, filed on Dec. 18, 2013.

(51) Int. Cl.
*A61M 16/08* (2006.01)
*A61M 16/20* (2006.01)
(Continued)

(52) U.S. Cl.
CPC .... *A61M 16/0816* (2013.01); *A61M 16/0057* (2013.01); *A61M 16/06* (2013.01);
(Continued)

(58) Field of Classification Search
CPC ...... A61M 16/00; A61M 16/06; A61M 16/08; A61M 16/0816; A61M 16/0833;
(Continued)

(56) References Cited

U.S. PATENT DOCUMENTS

| 4,615,359 A | * | 10/1986 | Affa | F16L 59/07 138/104 |
| 4,691,741 A | * | 9/1987 | Affa | F16L 59/07 138/113 |

(Continued)

FOREIGN PATENT DOCUMENTS

| WO | WO2007045008 A1 | 4/2007 |
| WO | WO2010067237 A2 | 6/2010 |
| WO | WO2013068911 A1 | 5/2013 |

*Primary Examiner* — Rachel T Sippel
*Assistant Examiner* — Benjamin M. Kusiak
(74) *Attorney, Agent, or Firm* — Michael W. Haas (57) ABSTRACT

An fluid connector apparatus having an exhalation insert that provides an improved exhalation feature whereby exhaled breathing gas flows out of the fluid connector apparatus in the form of elongated blades of gas. The elongated blades of gas enable improved fluid flow when compared with conventional circular jets of gas and advantageously also entrain atmospheric gases adjacent the gas blades to facilitate diffusion and dissipation of the gas blades. The fluid connector apparatus includes one or more elongated flow channels formed between the exhalation insert and the fluid connector. The exhaust gas flows through the flow channels, and the flow channels cause the discharged gas to be output in the form of the elongated blades of gas. The exhalation feature enables the outputting of exhaled breathing gas in greater volumes, at reduced velocities, and with reduced acoustic signature.

11 Claims, 13 Drawing Sheets

(51) Int. Cl.
*A61M 16/00* (2006.01)
*A61M 16/06* (2006.01)

(52) U.S. Cl.
CPC ....... *A61M 16/208* (2013.01); *A61M 2205/42* (2013.01); *A61M 2206/11* (2013.01)

(58) Field of Classification Search
CPC .............. A61M 16/0825; A61M 16/20; A61M 16/208; A61M 16/209; A61M 16/0875; A61M 16/0883; A61M 2016/0661
USPC .... 138/39, 113, 92, 94; 128/205.24, 204.18, 128/206.26; 137/115.12, 855
See application file for complete search history.

(56) References Cited

U.S. PATENT DOCUMENTS

| | | | | |
|---|---|---|---|---|
| 6,464,261 | B1 * | 10/2002 | Dybevik | E21B 17/042 285/123.15 |
| 6,561,190 | B1 * | 5/2003 | Kwok | A61M 16/06 128/204.18 |
| 6,561,191 | B1 * | 5/2003 | Kwok | A61M 16/06 128/205.11 |
| 6,581,594 | B1 * | 6/2003 | Drew | A61M 16/06 128/204.18 |
| 8,522,784 | B2 * | 9/2013 | Ng | A61M 16/06 128/206.28 |
| 9,174,018 | B2 * | 11/2015 | Ho | A61M 16/06 |
| 9,254,370 | B2 * | 2/2016 | Lynch | A61M 16/06 |
| 9,579,478 | B2 * | 2/2017 | Matula | A61M 16/06 |
| 10,086,160 | B2 * | 10/2018 | Burnham | A61M 16/06 |
| 10,265,496 | B2 * | 4/2019 | Bugamelli | A61M 16/208 |
| 2007/0107723 | A1 * | 5/2007 | Berg | A61M 16/047 128/200.26 |
| 2009/0050156 | A1 * | 2/2009 | Ng | A61M 16/06 128/205.24 |
| 2010/0236549 | A1 * | 9/2010 | Selvarajan | A61M 16/06 128/202.22 |
| 2012/0266884 | A1 * | 10/2012 | Ho | A61M 16/06 128/205.25 |
| 2014/0305433 | A1 * | 10/2014 | Rothermel | A61M 16/06 128/202.27 |
| 2014/0311496 | A1 * | 10/2014 | Rothermel | A61M 16/06 128/206.24 |

\* cited by examiner

FLUID CONNECTOR WITH EXHAUST VALVE

CROSS-REFERENCE TO RELATED APPLICATIONS

This patent application claims the priority benefit under 35 U.S.C. § 371 of international patent application no. PCT/IB2014/066541, filed Dec. 3, 2014, which claims the priority benefit under 35 U.S.C. § 119(e) of U.S. Provisional Application No. 61/917,611 filed on Dec. 18, 2013, the contents of which are herein incorporated by reference.

BACKGROUND OF THE INVENTION

1. Field of the Invention

The disclosed and claimed concept relates generally to devices that provide respiratory therapy to a patient and, more particularly, to an exhalation valve of a fluid connector that connects together a source of breathing gas and a patient interface in order to provide respiratory therapy to a patient.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 times per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive respiratory therapies such as ventilation and pressure support therapies involve the placement of a patient interface device, which is typically a nasal or nasal/oral mask, on the face of a patient to interface a source of breathing gas such as a ventilator or pressure support system in fluid communication with the airway of the patient so that a flow of breathing gas can be delivered from the pressure/flow generating device to the airway of the patient.

Typically, patient interface devices include a mask shell or frame having a cushion attached to the shell that contacts the skin of the patient. The mask shell and cushion are held in place by a headgear that wraps around the head of the patient. The mask and headgear form the patient interface assembly. A typical headgear includes flexible, adjustable straps that extend from the mask to attach the mask to the patient.

There are numerous situations where it is necessary or desirable to deliver a flow of breathable gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome, in particular, obstructive sleep apnea (OSA), or congestive heart failure.

A fluid connector such as an entrainment elbow is typically mounted to the patient interface device and is connectable with a flexible hose that extends to the source of breathing gas. Fluid connectors such as the aforementioned entrainment elbow are typically highly complex and require three or more directions of draw during an injection molding process and may further include other components that may be separately molded and then ultrasonically welded or otherwise attached to the elbow to form the fluid connector.

Such fluid connectors typically include an atmospheric opening that can be covered by a silicone flapper that enables the patient to breath air from the atmosphere in the event that the source of breathing gas should fail for some reason. Such fluid connectors typically additionally include some type of exhalation feature that permits exhaled air to be discharged from the elbow in order to permit flushing of the fluid passage that extends generally between the source of breathing gas and the patient's airways. Such an exhalation feature has typically been in the form of a number of small holes formed in the fluid connector that permit exhaled air to be exhausted therethrough. While a greater number of relatively smaller holes can result in quieter exhaust flow, it has been known that the extent to which such holes can be reduced in size is limited due to shortcomings in manufacturing reliability. It thus would be desirable to provide an improved exhalation feature.

SUMMARY OF THE INVENTION

An improved fluid connector apparatus having an improved exhalation insert provides an improved exhalation feature whereby exhaled breathing gas flows out of the fluid connector apparatus in the form of elongated blades of gas. The elongated blades of gas enable improved fluid flow when compared with conventional circular jets of gas and advantageously also entrain atmospheric gases adjacent the gas blades to facilitate diffusion and dissipation of the gas blades. The fluid connector apparatus includes one or more elongated flow channels that are formed between the exhalation insert and the fluid connector. The exhaust gas flows through the flow channels, and the flow channels cause the discharged gas to be output in the form of the elongated blades of gas. The exhalation feature thus enables the outputting of exhaled breathing gas in greater volumes, at reduced velocities, and with reduced acoustic signature, all of which are desirable.

Accordingly, an aspect of the disclosed and claimed concept is to provide an improved exhalation insert that is cooperable with a fluid connector and that provides an exhalation feature whereby exhaust gases flow through elongated flow channels formed between the exhalation insert and the fluid connector in order to cause the gas that is output to be discharged in the form of elongated blades of gas which provide improved performance.

Another aspect of the disclosed and claimed concept is to provide an improved fluid connector apparatus that employs the aforementioned improved exhalation insert.

A further aspect of the disclosed and claimed concept is to provide an improved respiratory therapy apparatus that employs the aforementioned improved fluid connector apparatus.

As such, an aspect of the disclosed and claimed concept is to provide an improved exhalation insert that is structured to be at least partially received in a receptacle that is formed in a fluid connector and that is in communication with an interior region of the fluid connector, the fluid connector being structured to connect together a patient interface device and a source of breathing gas which are structured to provide respiratory therapy to a patient. The exhalation insert can be generally stated as including a support that can be generally stated as including a peripheral wall that includes a peripheral surface, a mounting apparatus that can be generally stated as including at least a first abutment situated on the peripheral wall and protruding outwardly away from the peripheral surface, the at least first abutment having at least a first edge surface that extends from the peripheral surface and an engagement surface that extends from the at least first edge surface, at least a portion of the support and at least a portion of the mounting apparatus being structured to be received in the receptacle formed in the fluid connector, the engagement surface being structured to be engaged with a portion of a lateral surface of the fluid connector that is situated adjacent the receptacle, and the at least first edge surface and at least a portion of the peripheral surface that extends from the at least first edge surface together being structured to be cooperable with a confronting portion of the lateral surface to form at least a portion of a flow channel that is disposed between a portion of the support and a portion of the fluid connector and that is structured to enable fluid communication between the interior of the fluid connector and the atmosphere.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
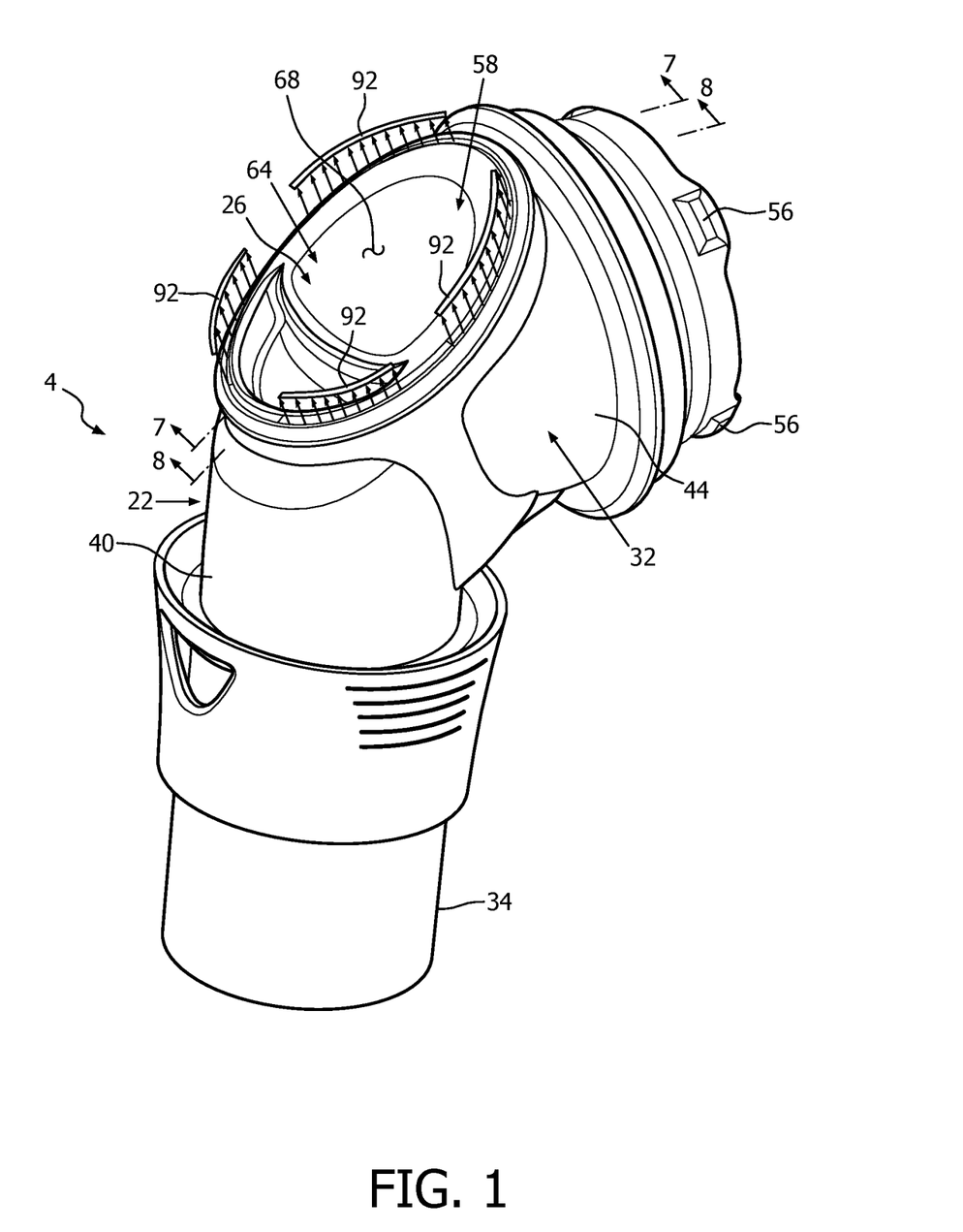
FIG. 1 is a perspective view of an improved fluid connector apparatus in accordance with a first embodiment of the disclosed and claimed concept.
Figure 2:
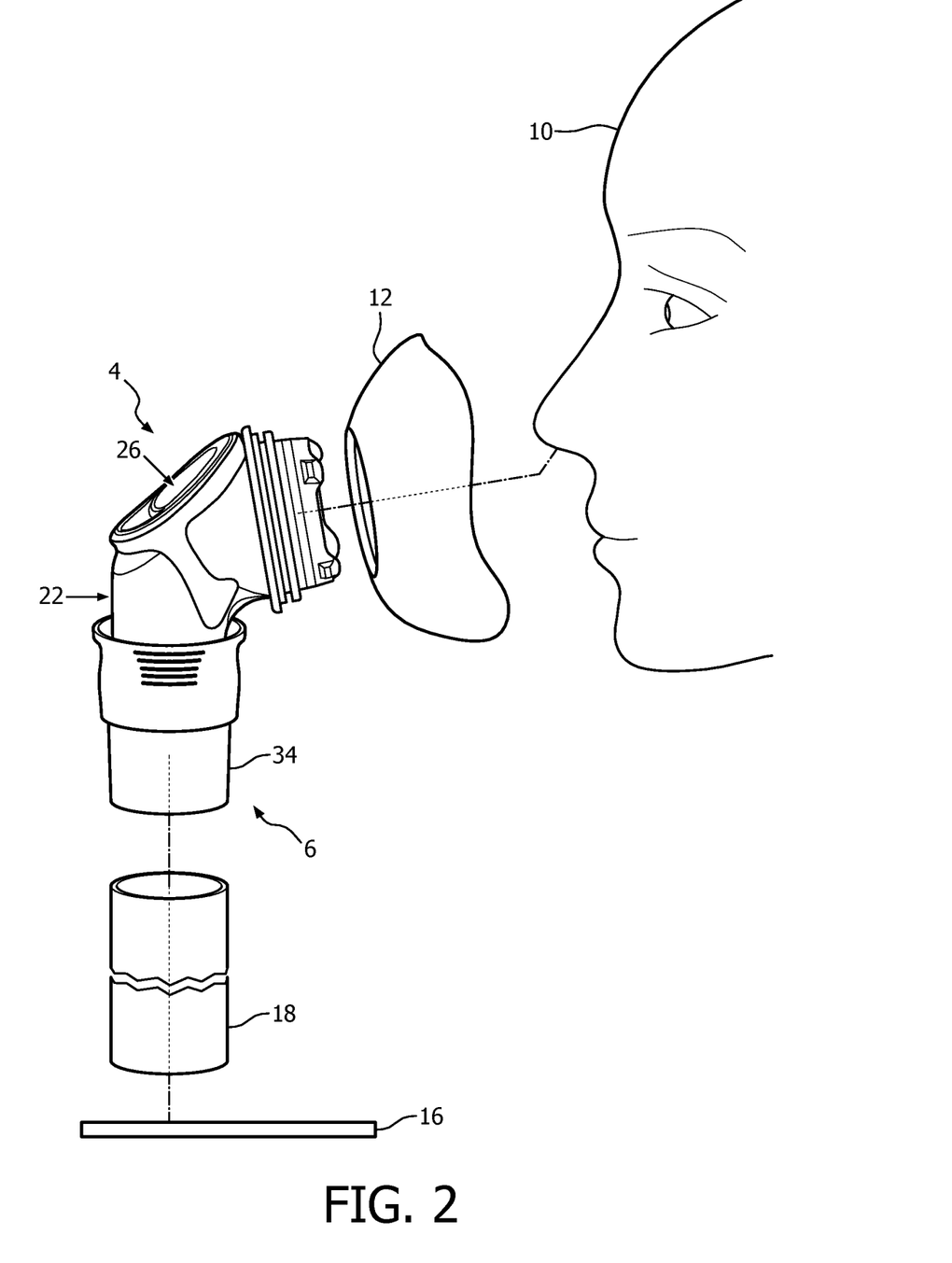
FIG. 2 is a schematic depiction of an improved respiratory therapy apparatus that employs the fluid connector apparatus of FIG. 1.

An improved fluid connector apparatus 4 in accordance with a first embodiment of the disclosed and claimed concept is depicted generally in FIGS. 1-11. Fluid connector apparatus 4 is advantageously employable in an improved respiratory therapy apparatus 6 that is depicted in FIG. 2 as providing respiratory therapy to a patient 10. Respiratory therapy apparatus 6 of FIG. 2 can be said to include a schematically depicted interface device 12 which may be, by way of example, a nasal or nasal/oral mask or other such device that is suited to patient 10. Fluid connector apparatus 4 places interface device 12 in fluid communication with a source of breathing gas 16 such as a CPAP machine or other such source of breathing gas. A supply hose 18 typically extends between source of breathing gas 16 and fluid connector apparatus 4.

Figure 3:
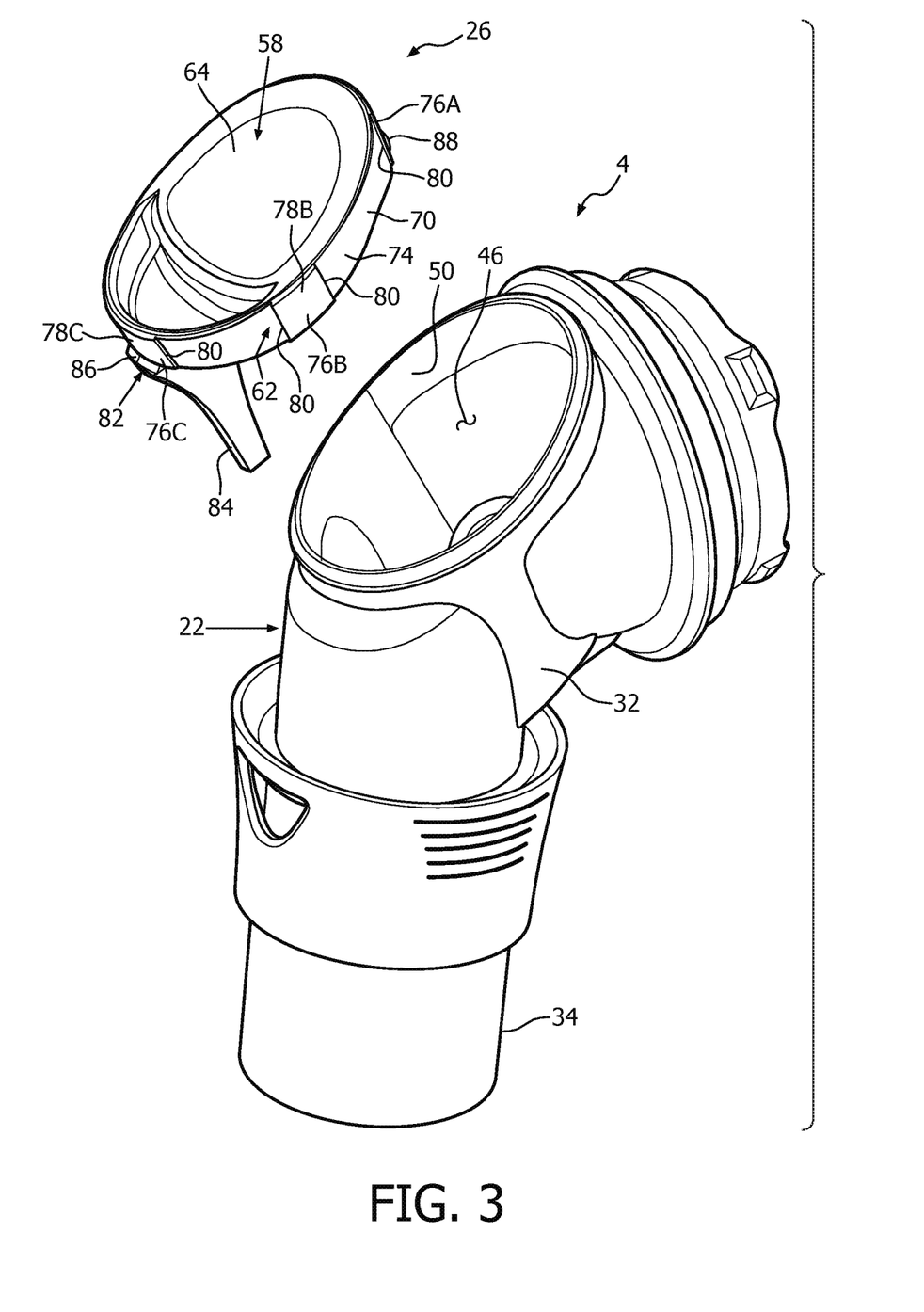
FIG. 3 is an exploded view of the fluid connector apparatus of FIG. 1.
Figure 4:
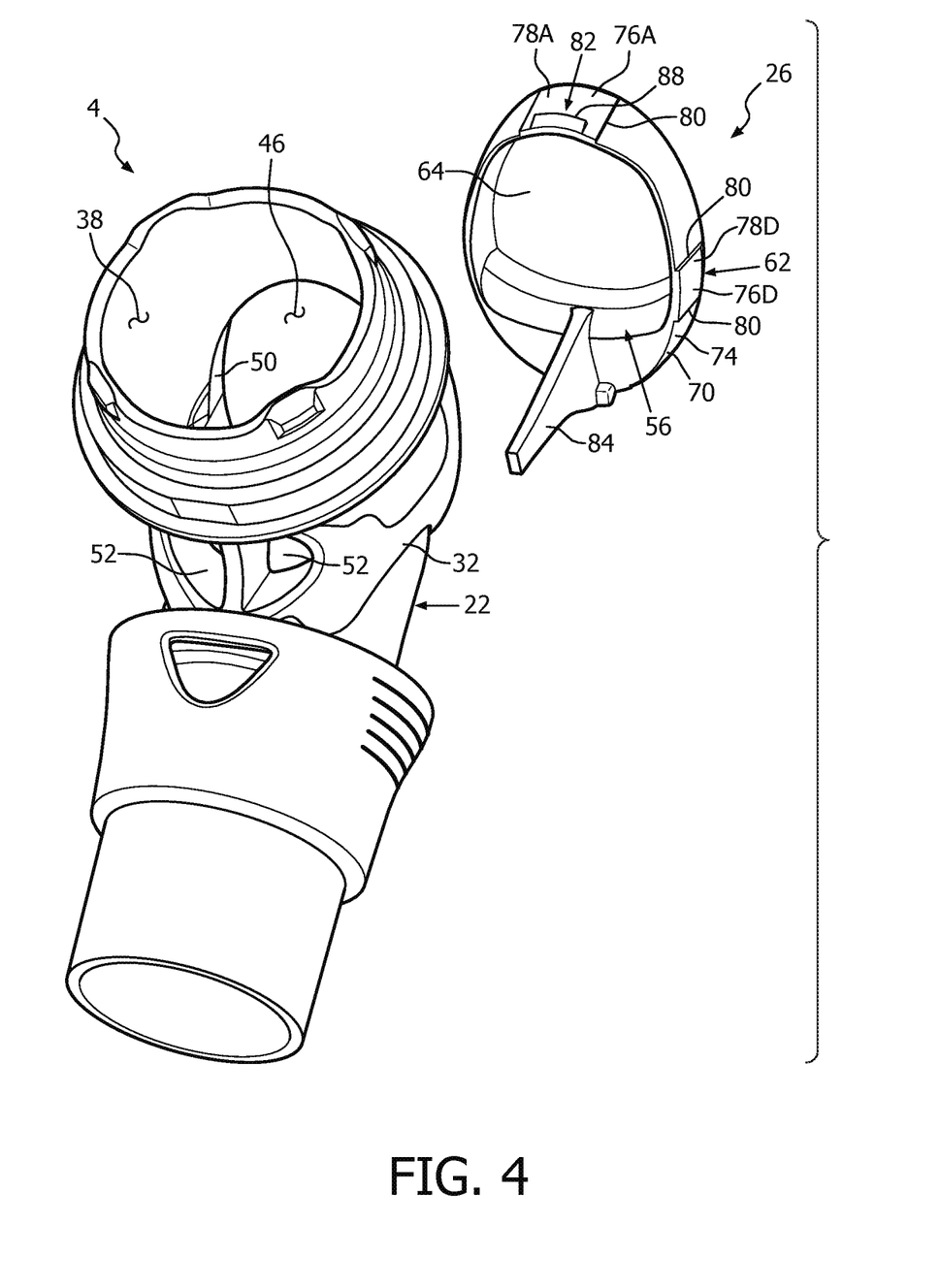
FIG. 4 is another exploded view of the fluid connector apparatus of FIG. 1.
Figure 5:
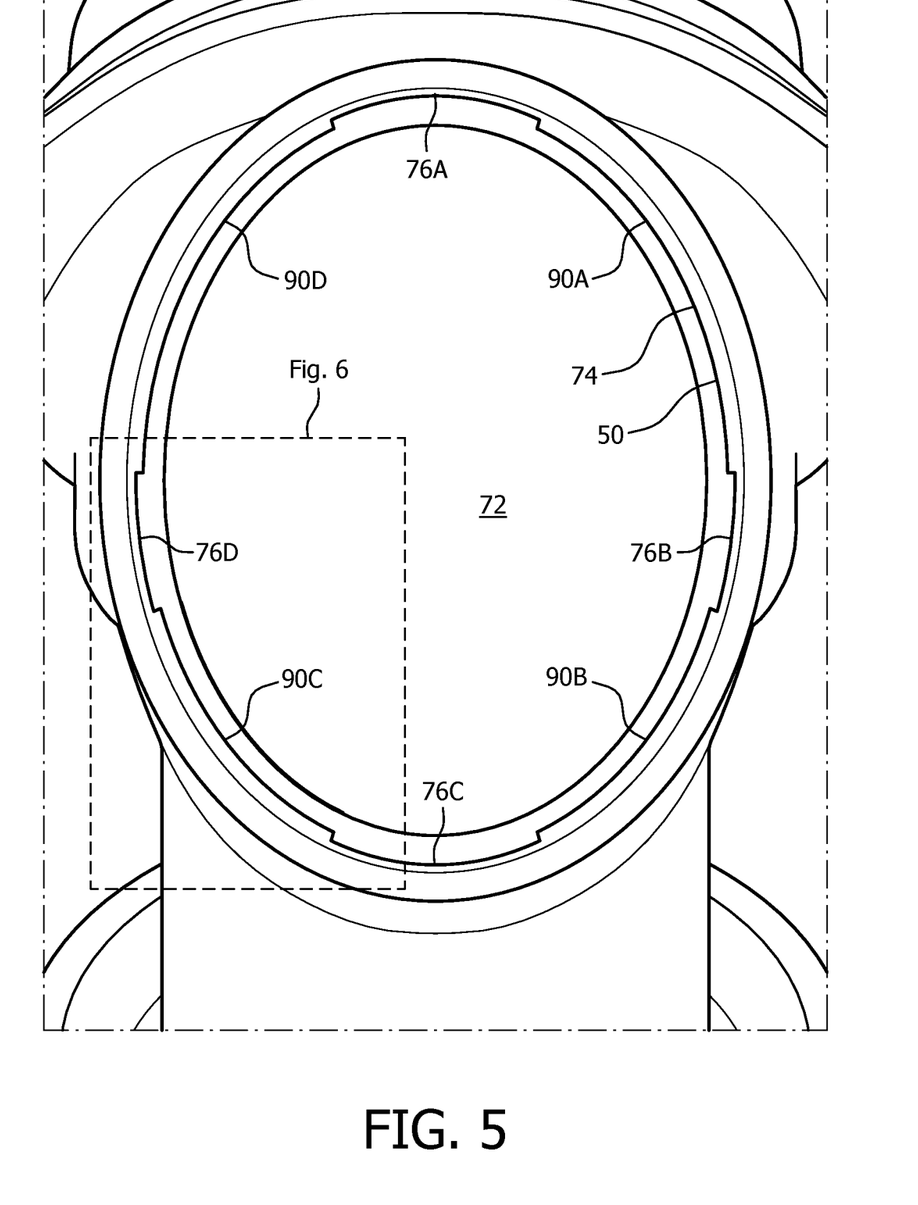
FIG. 5 is a top view of the fluid connector apparatus of FIG. 1.
Figure 6:
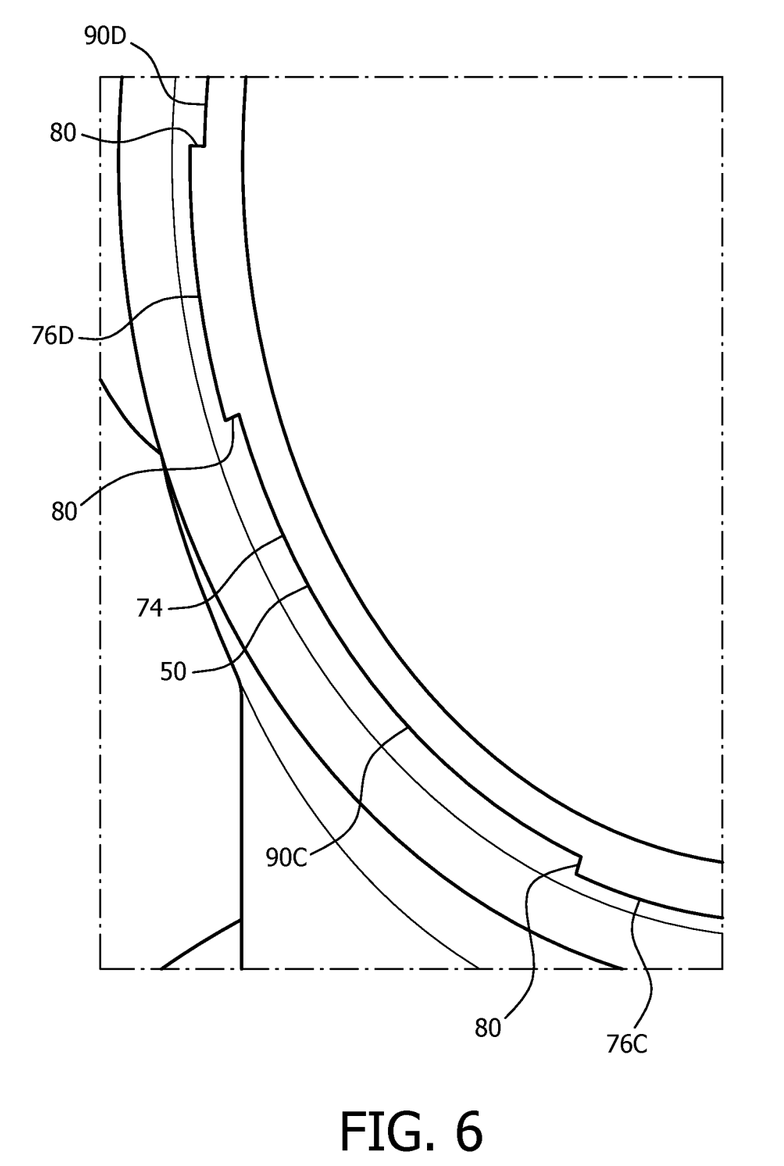
FIG. 6 is an enlarged depiction of the enclosed portion of FIG. 5.

As can be understood from FIGS. 3 and 4, fluid connector apparatus 4 can be said to include a fluid connector 22 and an improved exhalation insert 26 in accordance with an aspect of the disclosed and claimed concept. Fluid connector apparatus 4 additionally includes a flapper 28 that is depicted generally in FIGS. 7 and 9 and which is a flexible valve-like element that will be described in greater detail below.

Fluid connector 22 can be said to include a body 32 that is hollow and that has an interior region 38 formed therein. Fluid connector 22 can further be said to include a swivel component 34 that is pivotably situated on a supply leg 40 of body 32 and that is connectable with an end of supply hose 18. Body 32 further includes an interface leg 44 opposite supply leg 40.

Body 32 has formed therein a receptacle 46 that is of a generally elliptical or other arcuate shape and that is in communication with interior region 38. Body 32 further includes a lateral surface 50 that is adjacent receptacle 46. Body 32 can further be said to have an atmospheric opening 52 formed therein that is in communication with the atmosphere and which enables air from the atmosphere to be drawn into interior region 38 as a result of normal breathing of patient 10 in the event of a failure of source of breathing gas 16. In this regard, atmospheric opening 52 provides fluid communication between interior region 38 and the atmosphere, with such fluid communication being regulated by flapper 28. More particularly, when a fluid pressure that is in excess of atmospheric pressure is experienced within interior region 38, such as when source of breathing gas 16 provides a flow of breathing gas to patient 10, such increased fluid pressure causes flapper 28 to deflect and cover atmospheric opening 52, thereby enabling the flow of breathing gas to be therapeutically provided to patient 10 rather than flowing directly out of atmospheric opening 52.

It can be seen that receptacle 46 and atmospheric opening 52 are generally aligned with one another or at least partially overlie one another. This is advantageous because it permits a single draw during injection molding to form both receptacle 46 and atmospheric opening 52, which advantageously reduces cost.

Supply and interface legs 40 and 44 give to body 32 a generally elbow-like shape. Interface leg 44 has one or more lugs 56 situated thereon that enable a pivotable connection of fluid connector apparatus 4 with interface device 12.

Exhalation insert 26 can be said to include a support 58 and a mounting apparatus 62 that is situated on support 58. Support 58, in the depicted exemplary embodiment, can be said to include a central structure 64 having an exterior surface 68 and as further including a peripheral wall 70 having a peripheral surface 74. In the depicted exemplary embodiment, central structure 64 is formed with an indentation 72 to which a brace 84 of support 58 is mounted. Exterior surface 68 is depicted herein as being generally flat and slightly curved, as can be understood best from FIG. 10. Exterior surface 68 faces in a direction generally away from fluid connector 22 when exhalation insert 26 is mounted thereon. Peripheral surface 74 is of a generally elliptical or otherwise arcuate shape.

Mounting apparatus 62 can be said to include a plurality of abutments 76A, 76B, 76C, and 76D, which may be collectively or individually referred to herein with the numeral 76. Abutments 76 are situated on peripheral wall 70 and protrude outwardly from peripheral surface 74. Abutments 76 each include an engagement surface 78A, 78B, 78C, and 78D which may be collectively or individually referred to herein with the numeral 78. Engagement surfaces 78 are radially outwardly offset outwardly from peripheral surface 74 and each face in a direction generally away from peripheral wall 70. In the depicted exemplary embodiment, engagement surfaces 78 are likewise of a generally partially elliptical or otherwise arcuate shape. Abutments 76 each include a pair of abutment edges that are in the form of surfaces that are indicated generally at the numeral 80 herein for purposes of simplicity of disclosure. Abutment edges 80 can be said to extend generally between peripheral surface 74 and engagement surfaces 78.

Support 58 can further be said to include the aforementioned brace 84, and to further include a retention apparatus 82 that is situated on peripheral wall 70 at a location generally opposite exterior surface 68. Retention apparatus 82 includes a latch 86 that is formed on brace 84 and another latch 88 situated generally on abutment 76A opposite latch 86. Latches 86 and 88 are engagable with an interior surface of body 32, as is depicted generally in FIG. 7.

Figure 7:
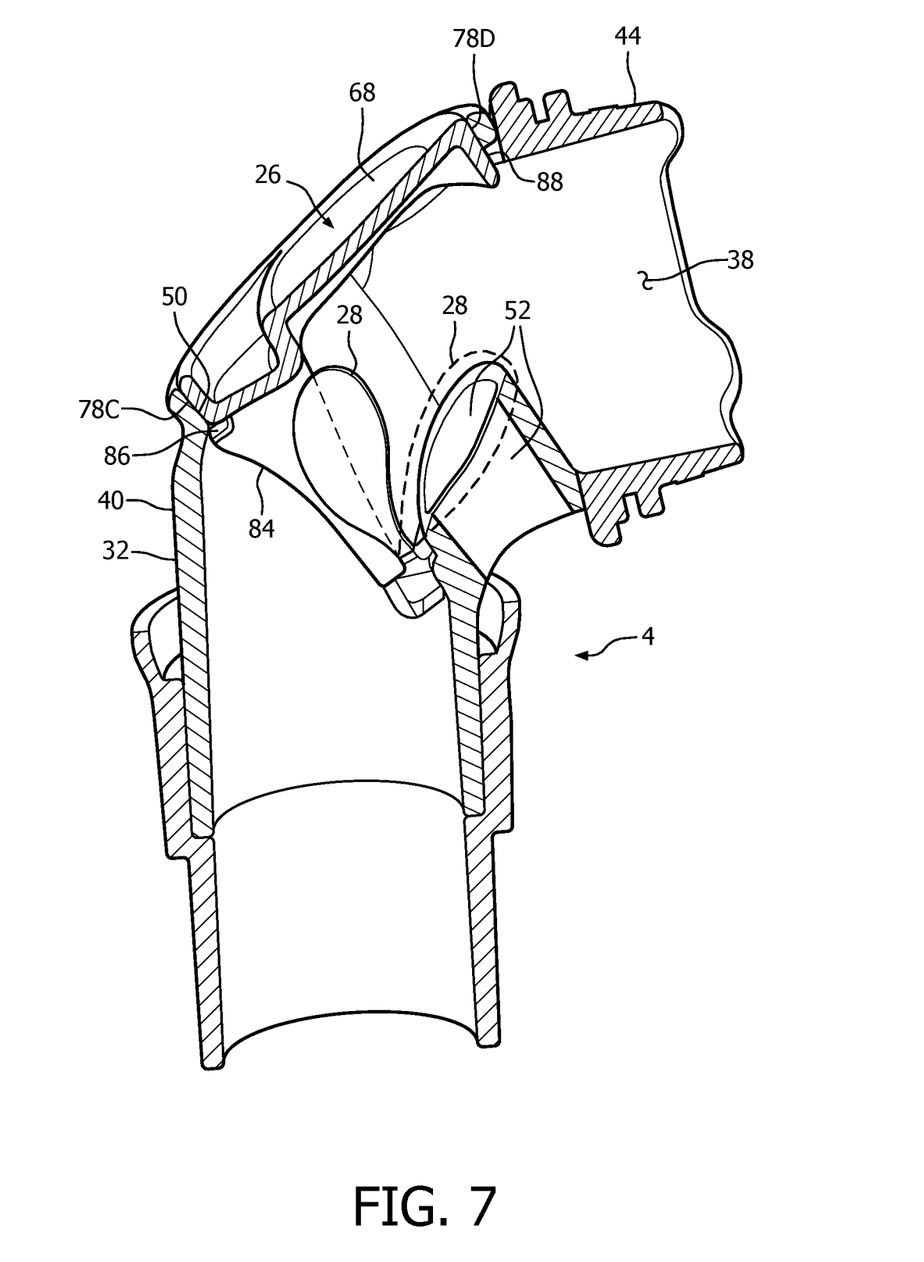
FIG. 7 is sectional view as taken along line 7-7 of FIG. 1.
Figure 8:
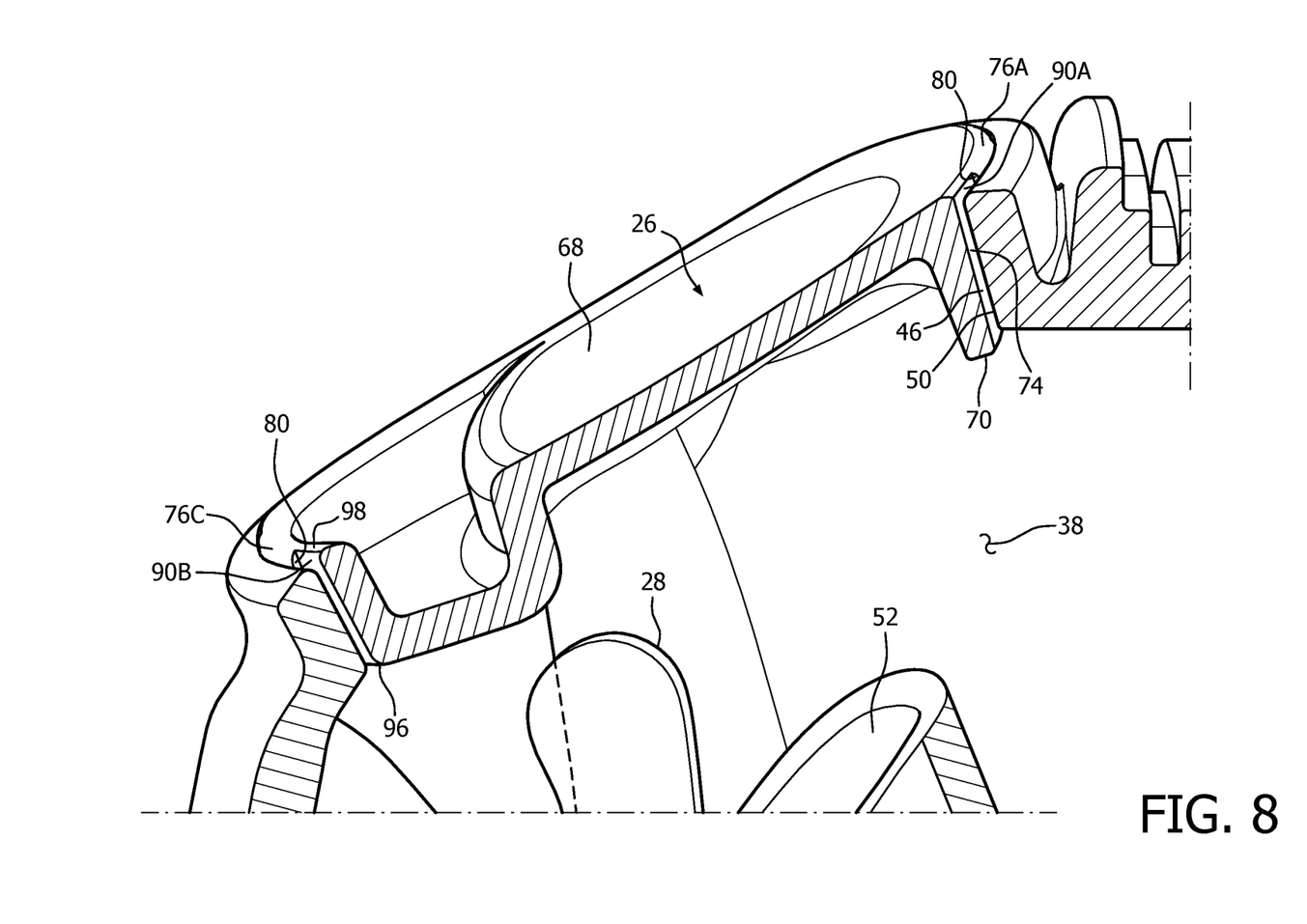
FIG. 8 is a sectional view as taken along line 8-8 of FIG. 1.
Figure 9:
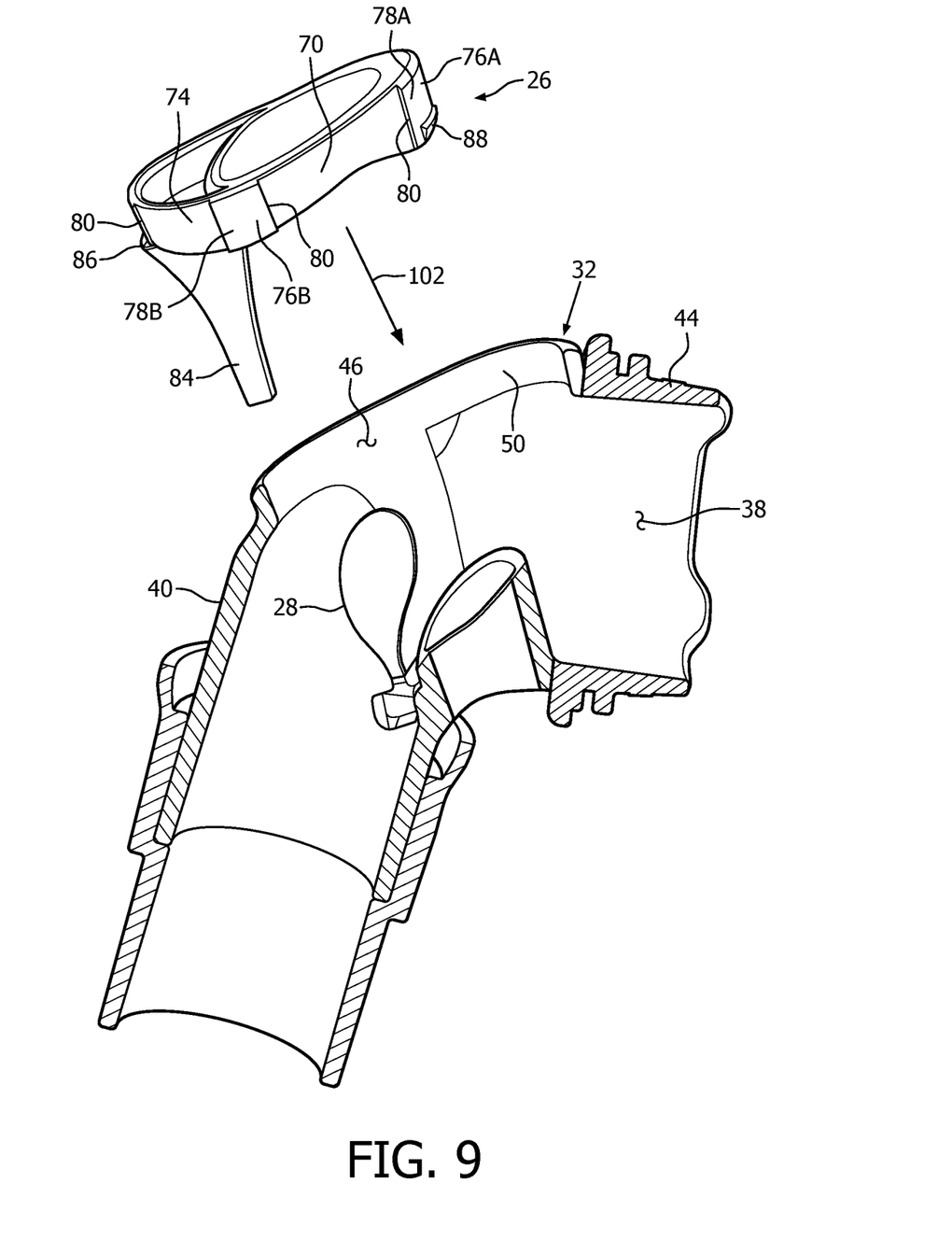
FIG. 9 is an exploded and partially sectioned depiction of the fluid connector apparatus of FIG. 1.

Brace 84 can be seen in FIG. 7 to protrude generally into interior region 38 and to engage flapper 28 or to be engageable therewith to resist flapper 28 from undesirably deflecting into the interior of supply leg 40. Flapper 28 is depicted in FIG. 9 as being in its free state, and it is therefore understood that flapper 28 is depicted in FIG. 7 as being at least partially deflected toward atmospheric opening 52 via its engagement with brace 84. FIG. 7 also depicts in dashed lines the position of flapper 28 overlying atmospheric opening 52, such as when a pressure in excess of atmospheric pressure is experienced within interior region 38.

In accordance with certain aspects of the disclosed and claimed concept, fluid connector apparatus 4 further includes a flow apparatus that can be said to include a plurality of flow channels 90A, 90B, 90C, and 90D, which may be collectively or individually referred to herein with the numeral 90. Flow channels 90 are formed between exhalation insert 26 and fluid connector 22 when the two are connected together, and flow channels 90 can each be said to extend generally between portions of peripheral and lateral surfaces 74 and 50 that confront one another and that extend between an adjacent pair of abutments 76. As such, flow channel 90A can be said to be bounded by abutment edges 80 of abutments 76A and 76B at the ends thereof and to be further bounded by a portion of peripheral surface 74 that extends between abutments 76A and 76B and a confronting portion of lateral surface 50 that confronts the aforementioned portion of peripheral surface 74 that extends between abutments 76A and 76B. In a like fashion, flow channel 90B can be said to extend between abutments 76B and 76C, flow channel 90C can be said to extend between abutments 76C and 76D, and flow channel 90D can be said to extend between abutments 76D and 76A, each of which additionally extends between a portion of peripheral surface 74 and a confronting portion of lateral surface 50 that extend between such adjacent pairs of abutments 76.

Exhalation insert 26 is mountable to fluid connector 22 to form fluid connector apparatus 4 by receiving brace 84 and retention apparatus 82 into receptacle 86 and receiving engagement surfaces 78 against lateral surface 50. This causes latches 86 and 88 to snap fit and to engage an interior surface of body 32 to retain engagement surfaces 78 against lateral surface 50. The engagement of engagement surfaces 78 with corresponding portions of lateral surface 50 retains exhalation insert 26 within receptacle 46 in the position depicted generally in FIG. 5 whereby flow channels 90 are each unblocked, i.e., open, and permit exhaust gas to flow therethrough from interior region 38 toward the atmosphere at the exterior of fluid connector apparatus 4. Since flow channels 90 are each of an elongated and narrow shape, such shape causes the gas that is exhausted therethrough to be exhausted in the form of a set of exhaust gas blades that are depicted in a schematic fashion in FIGS. 1 and 11 at the numeral 92.

Figure 11:
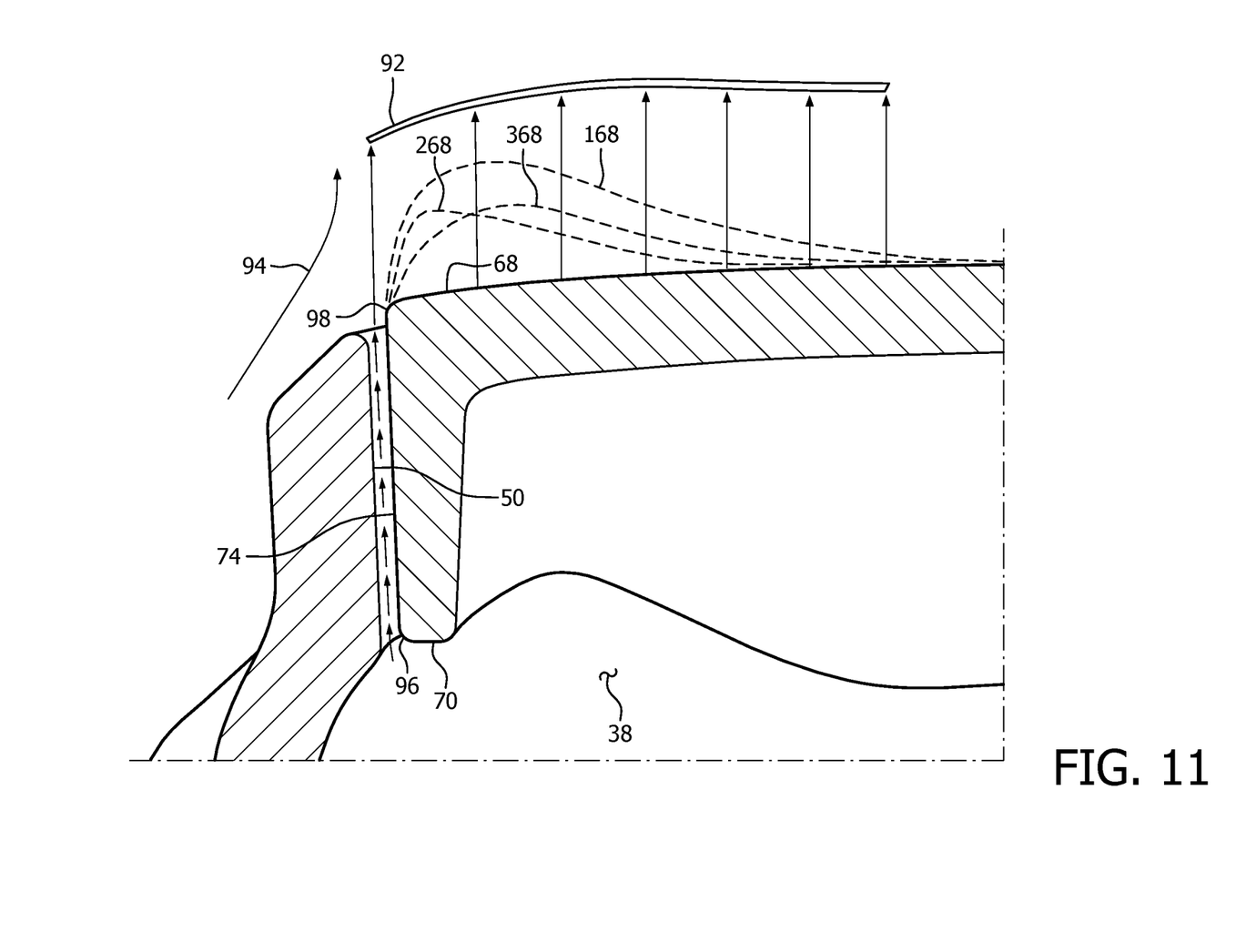
FIG. 11 is a schematic depiction of an exhaust gas blade that is discharged from the fluid connector apparatus and additionally depicts several alternative profiles that an exterior surface of the exhalation insert can take to provide different dissipation characteristics.

More particularly, FIG. 11 depicts exhaust gas blade 92 discharging into the atmosphere and as entraining an entrained portion 94 of the atmosphere in a region adjacent exhaust gas blade 92. That is, the flow of exhaust gas blades 92 into the atmosphere immediately outside of flow channels 90 causes the air surrounding exhaust gas blades 92 to be entrained with exhaust gas blades 92 due at least in part to the viscous and/or momentum properties of exhaust gas blade 92. Such entrainment of exhaust gas blade 92 with the atmosphere causes exhaust gas blade 92 to be relatively quickly dissipated, thereby resulting in a reduced acoustic signature and a reduced pressure or jetting signature. Additionally, the entrainment of exhaust gas blades 92 with entrained portions 94 of the atmosphere causes enhanced dissipation and diffusion of exhaust gas blades 92 into the atmosphere to provide reduced jetting properties at the exterior of fluid connector apparatus 4. This advantageously reduces the jetting effect on, for example, a bed partner.

Moreover, while in the depicted exemplary embodiment the space between the portions of lateral surface 50 and peripheral surface 74 that bound flow channels 90 is only on the order of 0.010 inches (0.25 millimeters) in size, it is noted that the size and shape of exhalation insert 26, as well as the distance between lateral surface 50 and peripheral surface 54 and the configuration of mounting apparatus 62, individually or in combination, can be altered to suit the needs of any particular application. Such alteration can be tailored to provide whatever flow capability is required depending upon the pressures at opposite ends of flow channels 90, the needed flow rates of exhaust gas, and other factors. As such, fluid connector apparatus 4 can be configured to provide flow channels 90 having any of a wide variety of desired flow properties.

Figure 10:
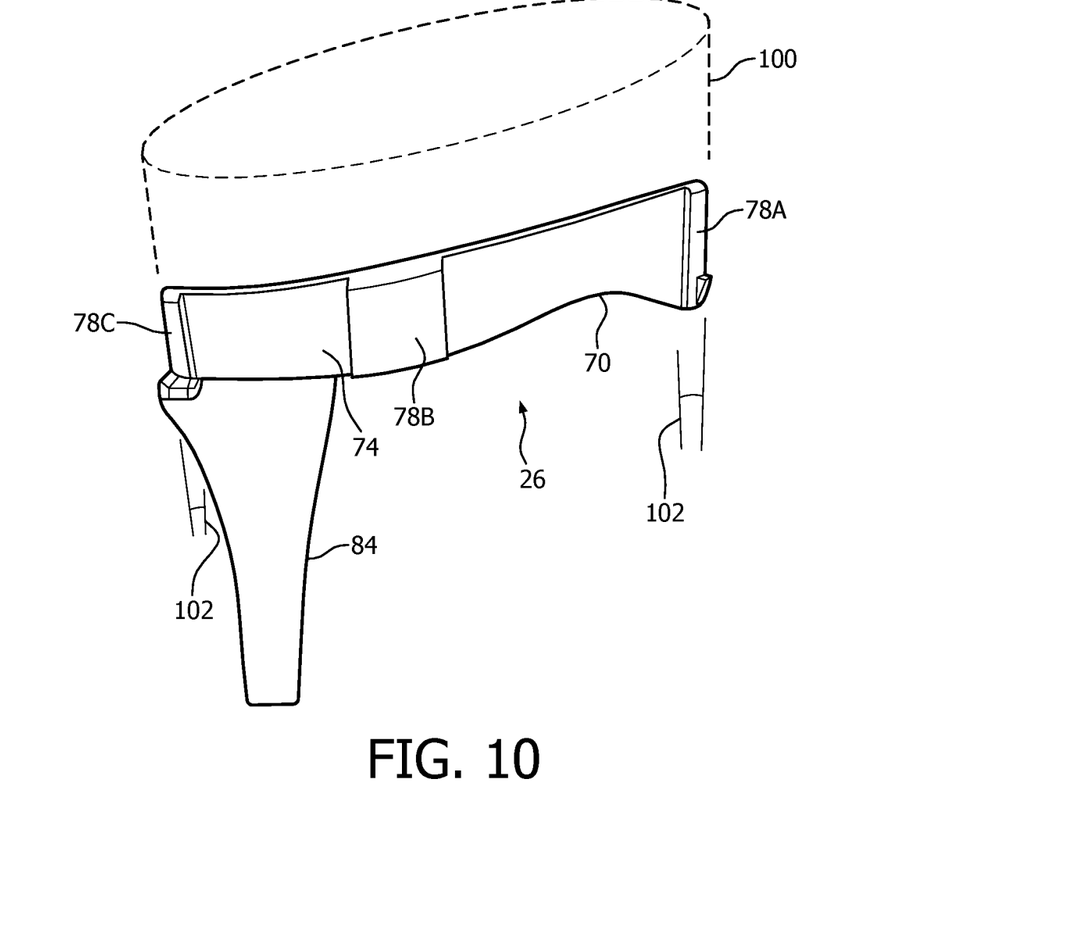
FIG. 10 is a side elevational view of the exhalation insert.

As can be understood from FIG. 10, engagement surfaces 78 are oriented oblique to one another and can be generally said to lie along the surface of an elliptical or non-elliptical cone 100. In the depicted exemplary embodiment, engagement surfaces 78 are oriented at approximately 5° (five degrees) in opposite directions away from a reference which, in the depicted exemplary embodiment, is represented by an insertion direction 102, which is the direction in which exhalation insert 26 is moved when being received into receptacle 46. It is understood that lateral surface 50 and peripheral surface 74 are likewise oriented at the same angle with respect to the same reference. The conic arrangement of engagement surfaces 78 and lateral surface 50 in combination with latches 86 and 88 securely retains exhalation insert 26 on fluid connector 22 in the orientation depicted generally in FIG. 5. This advantageously and reliably retains flow channels 90 in an open condition and maintains their intended and desired flow properties.

The flow of exhaust gas through flow channels 90 is depicted generally in FIG. 11 as beginning at a leading edge of peripheral wall 70 and as being discharged into the atmosphere at a trailing edge 98 of peripheral wall 70. In this regard, it is understood that leading edge 96 is situated generally adjacent or within interior region 38 whereas trailing edge 98 is situated adjacent or in the atmosphere. In this regard, therefore, it can be seen that various other modifications to the shapes, features, proportions, etc., of flow channels 90 themselves can be implemented to achieve desired entrainment and dissipation objective. The entrainment of entrained portions 94 of the atmosphere with exhaust gas blades 92 advantageously provides reduced pressure and acoustic signatures. Fluid connector apparatus 4 thus advantageously provides reliable flow channels 90 through which the exhaust gases are permitted to flow from interior region 38 to the atmosphere.

It is understood that such entrainment of entrained portions 94 of the atmosphere is at least in part affected by the shape of exterior surface 68. FIG. 11 additionally depicts a plurality of exemplary alternative exterior surfaces 168, 268, and 368 of alternate embodiments of exhalation insert 26 which can differently affect the entrainment of the atmosphere with exhaust gas blades 92. It thus can be understood that the exemplary profile of exterior surface 68 that is provided herein is merely for purposes of illustration, and it is therefore expressly noted that exhalation insert 26 could have any of exterior surfaces 168, 268, 368, or any combination thereof, or any other shape, depending upon the needs of the application.

Figure 12:
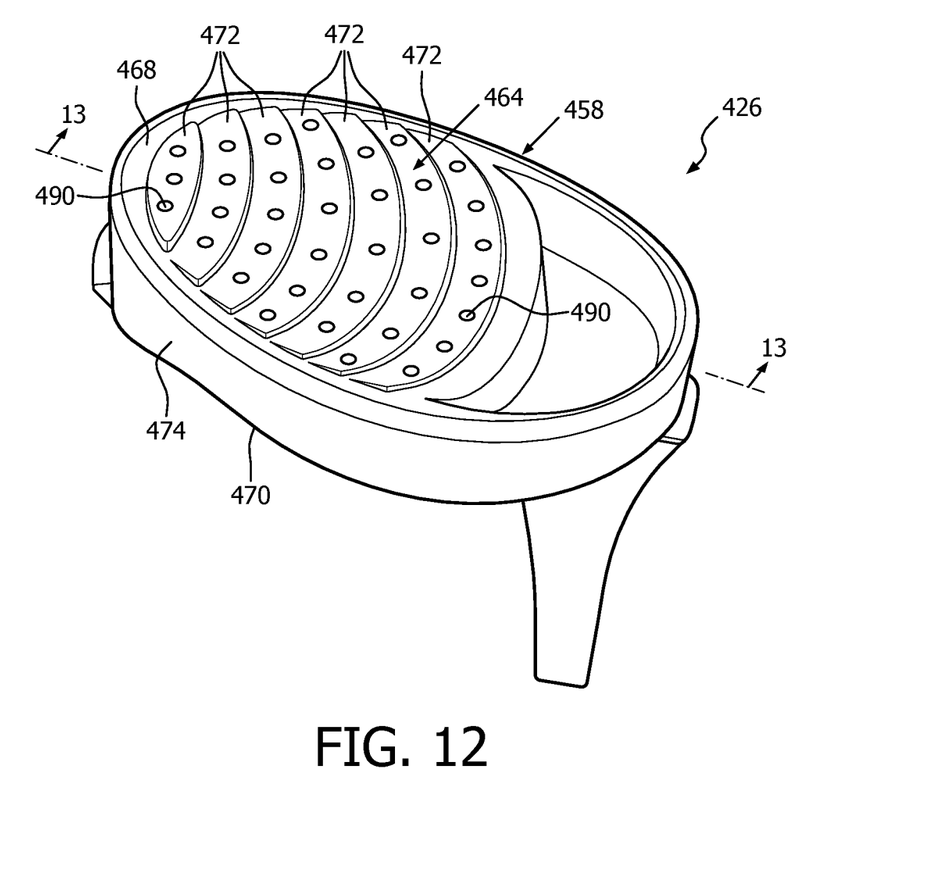
FIG. 12 is a perspective view of an improved exhalation insert in accordance with a second embodiment of the disclosed and claimed concept.
Figure 13:
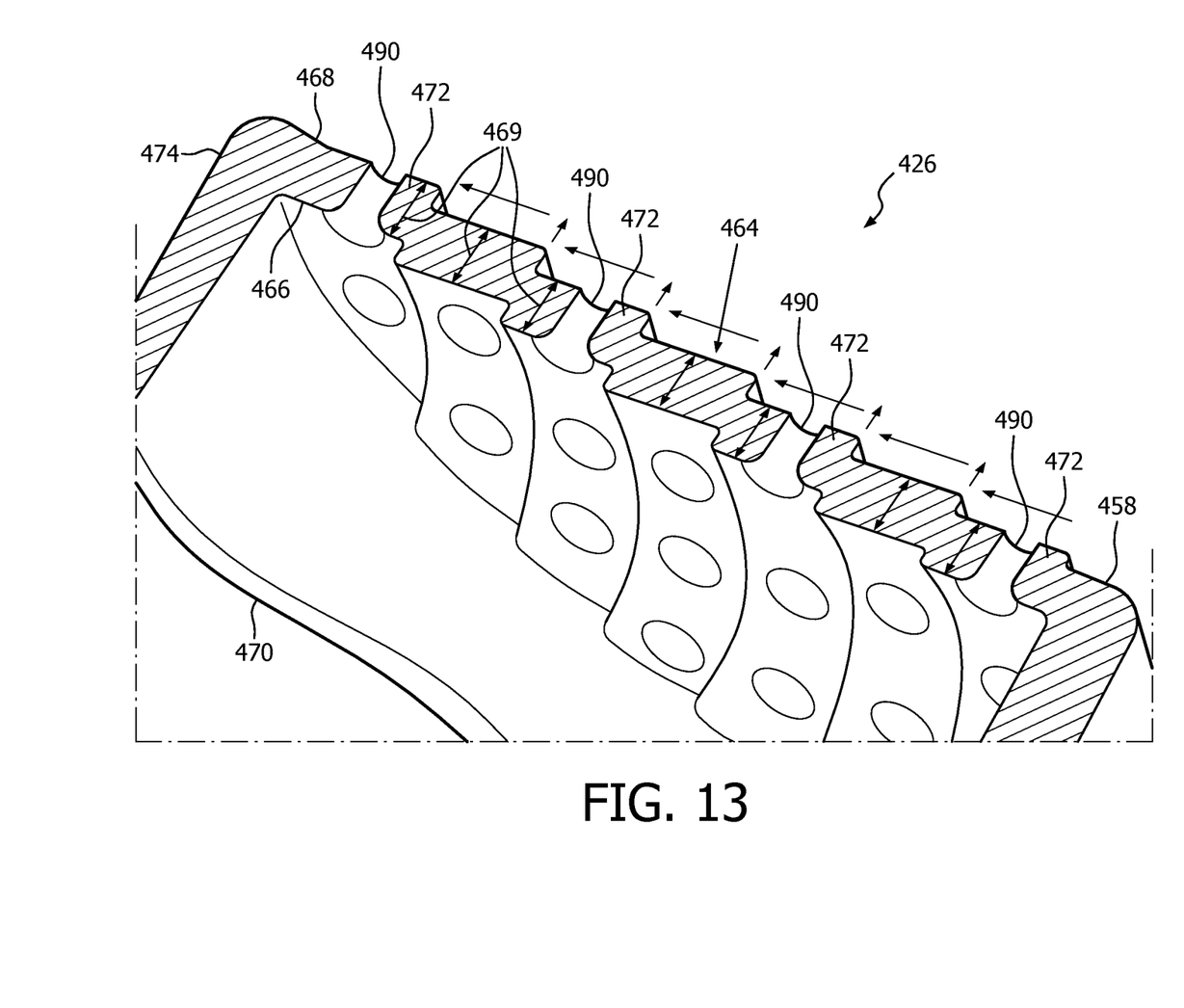
FIG. 13 is a sectional view as taken along line 13-13 of FIG. 12.

An improved exhalation insert 426 in accordance with a second embodiment of the disclosed and claimed concept is depicted generally in FIGS. 12 and 13. Exhalation insert 426 can be employed in place of exhalation insert 26 on fluid connector 22 to provide another improved connector apparatus in accordance with the disclosed and claimed concept. Exhalation insert 426 is similar to exhalation insert 26 except that it does not include mounting apparatus 62 or the resultant flow channels 90.

As can be seen in FIGS. 12 and 13, exhalation insert 426 includes a support 458 having a central structure 464 that has an interior surface 466 and an exterior surface 468. Central structure 464 includes a plurality of plate elements 472 that are positioned side-by-side in a terraced fashion to cause the various plate elements 472 to each be slightly offset from one another in a direction parallel with a thickness 469 of central structure 464.

Plate elements 472 are advantageously arranged to each have the same thickness 469 and to have one or more flow holes 490 formed therein that permit the flow of exhaust gas therethrough into communication with the atmosphere. Since each plate element 472 has the same thickness 469, flow holes 490 are each of substantially the same size and shape, and this facilitates the design and manufacture of tooling that forms exhalation insert 426 and flow holes 490. Flow holes 490 are depicted herein as being in the exemplary shape of a nozzle having a relatively wider cross section adjacent interior surface 466 and having a relatively narrower cross section adjacent exterior surface 468.

Exhalation insert 426 includes a peripheral wall 470 having a peripheral surface 474 that is configured to be received in receptacle 46 in substantially the same fashion as exhalation insert 426. It is noted, however, that the provision of flow holes 490 provides another mechanism by which exhaust gases can be permitted to flow to the atmosphere.

It is also expressly noted that the concepts of exhalation insert 426 can be applied to or combined with exhalation insert 26, such as by forming flow holes 490 in central structure 64 in addition to providing flow channels 90. Such a combined arrangement can provide even further flow rates and enhanced dissipation with further reduced acoustic and pressure signals, depending upon the needs of the particular application. Other variations will be apparent.

It is contemplated that any of the embodiments, combination of embodiments, or modification of embodiments of the disclosed concept described herein can be used by, for example and without limitation, a caregiver or technician, in the process of selecting a patient interface device for a patient.

The present invention contemplates that the exhalation insert can be either integral with the fluid connector or removable therefrom. If removable, the present invention contemplates that different configurations for the exhalation insert can be provided in the receptacle to select the amount of exhaust flow through the flow apparatus.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A fluid connector apparatus comprising:
   (a) a fluid connector including a first end, a second end, an interior region defined between the first end and the second end, and a receptacle defined in a wall of the fluid connector and in communication with the interior region of the fluid connector;
   (b) an exhalation insert structured to be at least partially received in the receptacle, the exhalation insert comprising:
       a support comprising a peripheral wall that includes a peripheral surface;
       a mounting apparatus comprising at least one abutment situated on the peripheral wall and protruding outwardly away from the peripheral surface, the at least one abutment having at least a first edge surface that extends from the peripheral surface and an engagement surface that extends from the at least first edge surface, at least a portion of the support and at least a portion of the mounting apparatus being structured to be received in the receptacle formed in the fluid connector, the engagement surface being structured to be engaged with a portion of a lateral surface of the fluid connector that is situated adjacent the receptacle; and
       the at least first edge surface and at least a portion of the peripheral surface that extends from the at least first edge surface together being structured to be cooperable with a confronting portion of the lateral surface to form at least a portion of a flow channel that is disposed between a portion of the support and a portion of the fluid connector and that is structured to enable fluid communication between the interior of the fluid connector and the atmosphere.

2. The fluid connector apparatus of claim 1, wherein the at least one abutment further comprises a plurality of abutments each having an engagement surface that is engaged with the lateral surface, to define a plurality of flow channels situated generally between the peripheral and lateral surfaces and between an adjacent pair of abutments of the plurality of abutments and that extend between the interior region and the atmosphere.

3. The fluid connector apparatus of claim 2, wherein the peripheral surface is generally arcuate, and wherein the engagement surfaces are angled with respect to one another and are disposed generally along an elliptical or non-elliptical cone.

4. The fluid connector apparatus of claim 1, wherein the support further comprises a central structure about which the peripheral wall extends, the central structure having an exterior surface that faces generally away from the fluid connector, the exterior surface being nonplanar at a location adjacent the flow channel and being structured to enhance diffusion of a flow of fluid out of the flow channel.

5. The fluid connector apparatus of claim 1, wherein the support comprises a central structure which comprises a plurality of plate elements that are arranged side-by-side and are each of substantially the same thickness and are offset from one another in a terraced fashion along the direction of the thicknesses thereof, and wherein at least some of the plate elements of the plurality of plate elements each has one or more flow holes formed therein that extend along the direction of the thickness and that are each of substantially the same size and shape.

6. The fluid connector apparatus of claim 5, wherein the one or more flow holes are of a nozzle shape having a relatively wider cross-section at an end thereof adjacent the interior region and having a relatively narrower cross-section at another end thereof adjacent the atmosphere.

7. The fluid connector apparatus of claim 1, wherein the fluid connector further has formed therein an opening that is situated on a wall opposite the receptacle and is generally aligned therewith, the opening being in fluid communication with the atmosphere.

8. The fluid connector apparatus of claim 7, further comprising a flexible flapper structured to overlie the opening when fluid at a pressure in excess of ambient pressure is present within the interior region, and wherein the support further comprises a brace that is disposed on at least one of the peripheral wall and a central structure of the support and extends into the interior region and that is structured to be engageable with the flapper to resist movement of the flapper a predetermined angular distance away from the opening.

9. The fluid connector apparatus of claim 1, wherein the support further comprises a retention apparatus that comprises at least a first latch that is engaged with the fluid connector and that is structured to retain the exhalation insert in a condition at least partially received in the receptacle.

10. The fluid connector apparatus of claim 9, wherein the peripheral wall includes a leading edge adjacent the interior region and a trailing edge situated generally at the exterior of the fluid connector, and wherein fluid flowing through the flow channel in a direction from the interior region toward the atmosphere flows in a direction generally from the leading edge toward the trailing edge, and wherein the at least first latch is situated at the leading edge of the peripheral wall.

11. The fluid connector apparatus of claim 1, wherein the exhalation insert is integral with the fluid connector.

* * * * *